US012673191B2

(12) United States Patent
Tamir et al.

(10) Patent No.: US 12,673,191 B2
(45) Date of Patent: Jul. 7, 2026

(54) REMOVABLE VOLUME INDICATOR FOR SYRINGE

(71) Applicant: EDWARDS LIFESCIENCES CORPORATION, Irvine, CA (US)

(72) Inventors: Ilan Tamir, Irvine, CA (US); Michael R. Bialas, Lake Forest, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 18/541,489

(22) Filed: Dec. 15, 2023

(65) Prior Publication Data

US 2024/0123200 A1 Apr. 18, 2024

Related U.S. Application Data

(62) Division of application No. 16/424,323, filed on May 28, 2019, now Pat. No. 11,844,914.

(60) Provisional application No. 62/680,980, filed on Jun. 5, 2018.

(51) Int. Cl.
*A61M 25/10* (2013.01)
*A61F 2/24* (2006.01)

(52) U.S. Cl.
CPC ..... *A61M 25/10188* (2013.11); *A61F 2/2433* (2013.01); *A61M 25/10182* (2013.11); *A61M 2205/3379* (2013.01)

(58) Field of Classification Search
CPC ................ A61F 2/2433; A61F 2/2427; A61M 25/10188; A61M 25/10182; A61M 5/178
See application file for complete search history.

(56) References Cited

U.S. PATENT DOCUMENTS

| | | | |
|---|---|---|---|
| 519,297 | A | 5/1894 | Bauer |
| 4,035,849 | A | 7/1977 | Angell et al. |
| 4,592,340 | A | 6/1986 | Boyles |
| 4,955,895 | A | 9/1990 | Sugiyama et al. |
| 4,994,077 | A | 2/1991 | Dobben |
| 5,059,177 | A | 10/1991 | Towne et al. |
| 5,176,698 | A | 1/1993 | Burns et al. |
| 5,192,297 | A | 3/1993 | Hull |
| 5,213,115 | A | 5/1993 | Zytkovicz et al. |
| 5,266,073 | A | 11/1993 | Wall |
| 5,325,845 | A | 7/1994 | Adair |
| 5,358,496 | A | 10/1994 | Ortiz et al. |
| 5,411,552 | A | 5/1995 | Andersen et al. |
| 5,554,185 | A | 9/1996 | Block et al. |
| 5,591,195 | A | 1/1997 | Taheri et al. |
| 5,599,305 | A | 2/1997 | Hermann et al. |

(Continued)

FOREIGN PATENT DOCUMENTS

| | | |
|---|---|---|
| CN | 103889485 A | 6/2014 |
| CN | 104135972 A | 11/2014 |

(Continued)

*Primary Examiner* — Brigid K Byrd
(74) *Attorney, Agent, or Firm* — Klarquist Sparkman LLP

(57) ABSTRACT

A volume indicator for a syringe can include an indicator body configured to removably clip onto a syringe body and a window portion extending through a thickness of the indicator body. The volume indicator can include inflation indicia corresponding to a range of expanded diameters for a prosthetic heart valve. The volume indicator can include one or more first engagement elements that correspond to one or more second engagement elements on a syringe.

21 Claims, 6 Drawing Sheets

(56)                References Cited

U.S. PATENT DOCUMENTS

| | | | |
|---|---|---|---|
| 5,632,760 A | 5/1997 | Sheiban et al. | |
| 5,639,274 A | 6/1997 | Fischell et al. | |
| 5,728,068 A | 3/1998 | Leone et al. | |
| 5,749,890 A | 5/1998 | Shaknovich | |
| 5,782,809 A | 7/1998 | Umeno et al. | |
| 5,797,930 A * | 8/1998 | Ovil | A61B 17/11 606/148 |
| 5,824,044 A | 10/1998 | Quiachon et al. | |
| 5,840,081 A | 11/1998 | Andersen et al. | |
| 5,908,405 A | 6/1999 | Imran et al. | |
| 5,916,147 A | 6/1999 | Boury | |
| 5,957,949 A * | 9/1999 | Leonhardt | A61F 2/07 606/198 |
| 5,961,536 A | 10/1999 | Mickley et al. | |
| 5,968,068 A | 10/1999 | Dehdashtian et al. | |
| 6,019,777 A | 2/2000 | Mackenzie | |
| 6,027,510 A | 2/2000 | Alt | |
| 6,033,381 A | 3/2000 | Kontos | |
| 6,143,016 A | 11/2000 | Bleam et al. | |
| 6,162,208 A | 12/2000 | Hipps | |
| 6,168,614 B1 | 1/2001 | Andersen et al. | |
| 6,174,327 B1 | 1/2001 | Mertens et al. | |
| 6,217,585 B1 | 4/2001 | Houser et al. | |
| 6,235,050 B1 | 5/2001 | Quiachon et al. | |
| 6,251,092 B1 | 6/2001 | Qin et al. | |
| 6,379,372 B1 | 4/2002 | Dehdashtian et al. | |
| 6,383,171 B1 | 5/2002 | Gifford et al. | |
| 6,454,799 B1 | 9/2002 | Schreck | |
| 6,458,153 B1 | 10/2002 | Bailey et al. | |
| 6,461,382 B1 | 10/2002 | Cao | |
| 6,471,672 B1 | 10/2002 | Brown et al. | |
| 6,500,147 B2 | 12/2002 | Omaleki et al. | |
| 6,514,228 B1 | 2/2003 | Hamilton et al. | |
| 6,527,979 B2 | 3/2003 | Constantz et al. | |
| 6,579,305 B1 | 6/2003 | Lashinski | |
| 6,582,462 B1 | 6/2003 | Andersen et al. | |
| 6,652,578 B2 | 11/2003 | Bailey et al. | |
| 6,730,118 B2 | 5/2004 | Spenser et al. | |
| 6,733,525 B2 | 5/2004 | Yang et al. | |
| 6,764,504 B2 | 7/2004 | Wang et al. | |
| 6,767,362 B2 | 7/2004 | Schreck | |
| 6,830,584 B1 | 12/2004 | Seguin | |
| 6,893,460 B2 | 5/2005 | Spenser et al. | |
| 6,908,481 B2 | 6/2005 | Cribier | |
| 7,011,094 B2 | 3/2006 | Rapacki et al. | |
| 7,018,406 B2 | 3/2006 | Seguin et al. | |
| 7,018,408 B2 | 3/2006 | Bailey et al. | |
| 7,137,993 B2 | 11/2006 | Acosta et al. | |
| 7,276,084 B2 | 10/2007 | Yang et al. | |
| 7,318,278 B2 | 1/2008 | Zhang et al. | |
| 7,320,702 B2 | 1/2008 | Hammersmark et al. | |
| 7,320,704 B2 | 1/2008 | Lashinski et al. | |
| 7,374,571 B2 | 5/2008 | Pease et al. | |
| 7,393,360 B2 | 7/2008 | Spenser et al. | |
| 7,435,257 B2 | 10/2008 | Lashinski et al. | |
| 7,510,575 B2 | 3/2009 | Spenser et al. | |
| 7,585,321 B2 | 9/2009 | Cribier | |
| 7,594,926 B2 | 9/2009 | Linder et al. | |
| 7,597,709 B2 | 10/2009 | Goodin | |
| 7,618,446 B2 | 11/2009 | Andersen et al. | |
| 7,780,723 B2 | 8/2010 | Taylor | |
| 7,785,366 B2 | 8/2010 | Maurer et al. | |
| 7,959,607 B2 | 6/2011 | Smit et al. | |
| 7,959,661 B2 | 6/2011 | Hijlkema et al. | |
| 8,029,556 B2 | 10/2011 | Rowe | |
| 8,167,932 B2 | 5/2012 | Bourang et al. | |
| RE43,882 E | 12/2012 | Hopkins et al. | |
| 8,449,606 B2 | 5/2013 | Eliasen et al. | |
| 8,475,523 B2 | 7/2013 | Duffy | |
| 8,568,472 B2 | 10/2013 | Marchand et al. | |
| 9,061,119 B2 | 6/2015 | Le et al. | |
| 9,119,716 B2 | 9/2015 | Lee et al. | |
| 9,795,477 B2 | 10/2017 | Tran et al. | |
| 2001/0002445 A1 | 5/2001 | Vesely | |
| 2001/0007082 A1 | 7/2001 | Dusbabek et al. | |
| 2002/0032481 A1 | 3/2002 | Gabbay | |
| 2002/0058995 A1 | 5/2002 | Stevens | |
| 2002/0088131 A1 | 7/2002 | Baxa et al. | |
| 2002/0165461 A1 | 11/2002 | Hayzelden et al. | |
| 2003/0040792 A1 | 2/2003 | Gabbay | |
| 2003/0050694 A1 | 3/2003 | Yang et al. | |
| 2003/0120341 A1 | 6/2003 | Shennib et al. | |
| 2004/0019323 A1 | 1/2004 | Carter et al. | |
| 2004/0093061 A1 | 5/2004 | Acosta et al. | |
| 2004/0133263 A1 | 7/2004 | Dusbabek et al. | |
| 2004/0143197 A1 | 7/2004 | Soukup et al. | |
| 2004/0186563 A1 | 9/2004 | Lobbi | |
| 2004/0186565 A1 | 9/2004 | Schreck | |
| 2004/0260389 A1 | 12/2004 | Case et al. | |
| 2005/0075724 A1 | 4/2005 | Svanidze et al. | |
| 2005/0080474 A1 | 4/2005 | Andreas et al. | |
| 2005/0096736 A1 | 5/2005 | Osse et al. | |
| 2005/0137689 A1 | 6/2005 | Salahieh et al. | |
| 2005/0149160 A1 | 7/2005 | McFerran | |
| 2005/0203614 A1 | 9/2005 | Forster et al. | |
| 2005/0203617 A1 | 9/2005 | Forster et al. | |
| 2005/0245894 A1 | 11/2005 | Zadno-Azizi | |
| 2006/0025857 A1 | 2/2006 | Bergheim et al. | |
| 2006/0173415 A1 | 8/2006 | Cummins | |
| 2006/0282150 A1 | 12/2006 | Olson et al. | |
| 2007/0005131 A1 | 1/2007 | Taylor | |
| 2007/0073389 A1 | 3/2007 | Bolduc et al. | |
| 2007/0088431 A1 | 4/2007 | Bourang et al. | |
| 2007/0112422 A1 | 5/2007 | Dehdashtian | |
| 2007/0129719 A1 | 6/2007 | Kendale et al. | |
| 2007/0203575 A1 | 8/2007 | Forster et al. | |
| 2007/0219612 A1 | 9/2007 | Andreas et al. | |
| 2007/0239254 A1 | 10/2007 | Chia et al. | |
| 2007/0244546 A1 | 10/2007 | Francis | |
| 2007/0265700 A1 | 11/2007 | Eliasen et al. | |
| 2008/0065011 A1 | 3/2008 | Marchand et al. | |
| 2008/0108952 A1 | 5/2008 | Horvath et al. | |
| 2008/0125853 A1 | 5/2008 | Bailey et al. | |
| 2008/0171995 A1 * | 7/2008 | Vitullo | A61M 5/28 604/187 |
| 2008/0294230 A1 | 11/2008 | Parker | |
| 2009/0005754 A1 | 1/2009 | Soetermans | |
| 2009/0024428 A1 | 1/2009 | Hudock, Jr. | |
| 2009/0069889 A1 | 3/2009 | Suri et al. | |
| 2009/0138079 A1 | 5/2009 | Tuval et al. | |
| 2009/0157175 A1 | 6/2009 | Benichou | |
| 2009/0192585 A1 | 7/2009 | Bloom et al. | |
| 2009/0228093 A1 | 9/2009 | Taylor et al. | |
| 2009/0276040 A1 | 11/2009 | Rowe et al. | |
| 2009/0281619 A1 | 11/2009 | Le et al. | |
| 2009/0299456 A1 | 12/2009 | Melsheimer | |
| 2009/0319037 A1 | 12/2009 | Rowe et al. | |
| 2010/0030318 A1 | 2/2010 | Berra | |
| 2010/0036472 A1 | 2/2010 | Papp | |
| 2010/0036473 A1 | 2/2010 | Roth | |
| 2010/0049313 A1 | 2/2010 | Alon et al. | |
| 2010/0076402 A1 | 3/2010 | Mazzone et al. | |
| 2010/0076541 A1 | 3/2010 | Kumoyama | |
| 2010/0082089 A1 | 4/2010 | Quadri et al. | |
| 2010/0094394 A1 | 4/2010 | Beach et al. | |
| 2010/0121425 A1 | 5/2010 | Shimada | |
| 2010/0145431 A1 | 6/2010 | Wu et al. | |
| 2010/0160894 A1 | 6/2010 | Julian et al. | |
| 2010/0161036 A1 | 6/2010 | Pintor et al. | |
| 2010/0174363 A1 | 7/2010 | Castro | |
| 2010/0198347 A1 | 8/2010 | Zakay et al. | |
| 2010/0274344 A1 | 10/2010 | Dusbabek et al. | |
| 2011/0015729 A1 | 1/2011 | Jimenez et al. | |
| 2011/0054596 A1 | 3/2011 | Taylor | |
| 2011/0137331 A1 | 6/2011 | Walsh et al. | |
| 2011/0160846 A1 | 6/2011 | Bishop et al. | |
| 2011/0313349 A1 | 12/2011 | Krulevitch et al. | |
| 2012/0041389 A1 | 2/2012 | Giambattista et al. | |
| 2012/0123529 A1 | 5/2012 | Levi et al. | |
| 2012/0239142 A1 | 9/2012 | Liu et al. | |
| 2013/0030519 A1 | 1/2013 | Tran et al. | |
| 2013/0261601 A1 | 10/2013 | Webler | |
| 2013/0268066 A1 | 10/2013 | Rowe | |
| 2013/0317598 A1 | 11/2013 | Rowe et al. | |

(56) References Cited

U.S. PATENT DOCUMENTS

| | | | |
|---|---|---|---|
| 2013/0338581 A1 | 12/2013 | Stevens et al. | |
| 2014/0074140 A1* | 3/2014 | Johnson | A61M 29/02 606/192 |
| 2014/0296962 A1 | 10/2014 | Cartledge et al. | |
| 2014/0296973 A1 | 10/2014 | Bergheim et al. | |
| 2014/0303565 A1* | 10/2014 | Kubo | A61M 3/00 604/208 |
| 2014/0336617 A1* | 11/2014 | Schaeffer | A61B 5/1076 604/100.02 |
| 2015/0080807 A1 | 3/2015 | Schneider et al. | |
| 2015/0080809 A1 | 3/2015 | Dasbach et al. | |
| 2015/0272733 A1 | 10/2015 | Le et al. | |
| 2015/0306318 A1 | 10/2015 | Lockhart et al. | |
| 2015/0320555 A1* | 11/2015 | Beith | A61F 2/2418 623/2.19 |
| 2016/0235458 A1 | 8/2016 | Roberts et al. | |
| 2016/0262920 A1 | 9/2016 | Green et al. | |
| 2017/0056149 A1 | 3/2017 | Rajpara et al. | |
| 2017/0065415 A1 | 3/2017 | Rupp et al. | |
| 2017/0354787 A1* | 12/2017 | Leary | A61M 5/3202 |
| 2018/0153689 A1 | 6/2018 | Maimon et al. | |
| 2018/0344456 A1 | 12/2018 | Barash et al. | |
| 2019/0117899 A1 | 4/2019 | Byskov et al. | |

FOREIGN PATENT DOCUMENTS

| | | | |
|---|---|---|---|
| DE | 19532846 A1 | 3/1997 | |
| DE | 19907646 A1 | 8/2000 | |
| EP | 0592410 B1 | 10/1995 | |
| EP | 0850607 A1 | 7/1998 | |
| FR | 2815844 A1 | 5/2002 | |
| KR | 20170136571 A | 12/2017 | |
| WO | 9117720 A1 | 11/1991 | |
| WO | WO-1992017221 A1 | 10/1992 | |
| WO | 9829057 A1 | 7/1998 | |
| WO | 9912483 A1 | 3/1999 | |
| WO | 0149213 A2 | 7/2001 | |
| WO | 0154625 A1 | 8/2001 | |
| WO | 0176510 A2 | 10/2001 | |
| WO | 0222054 A1 | 3/2002 | |
| WO | 0236048 A1 | 5/2002 | |
| WO | 0247575 A2 | 6/2002 | |
| WO | 02060352 | 8/2002 | |
| WO | 03030776 A2 | 4/2003 | |
| WO | 03047468 A1 | 6/2003 | |
| WO | 2004019825 A1 | 3/2004 | |
| WO | 2005084595 A1 | 9/2005 | |
| WO | 2006032051 A2 | 3/2006 | |
| WO | 2006111391 A1 | 10/2006 | |
| WO | 2006138173 A3 | 3/2007 | |
| WO | 2005102015 A3 | 4/2007 | |
| WO | 2007047488 A2 | 4/2007 | |
| WO | 2007067942 A1 | 6/2007 | |
| WO | 2008028569 A1 | 3/2008 | |
| WO | 2010098928 A1 | 9/2010 | |
| WO | 2010121076 A2 | 10/2010 | |
| WO | 2014088582 A1 | 6/2014 | |

* cited by examiner

REMOVABLE VOLUME INDICATOR FOR SYRINGE

CROSS-REFERENCE TO RELATED APPLICATION

This is a divisional application of U.S. patent application Ser. No. 16/424,323 filed on May 28, 2019, which application claims the benefit of U.S. Provisional Application 62/680,980 filed on Jun. 5, 2018, each of these applications being incorporated by reference herein in its entirety.

FIELD

The present disclosure relates to removable volume indicators for syringes, and particularly for syringes used to inflate balloon-expandable prosthetic heart valves.

BACKGROUND

Prosthetic cardiac valves have been used for many years to treat cardiac valvular disorders. The native heart valves (such as the aortic, pulmonary and mitral valves) serve critical functions in assuring the forward flow of an adequate supply of blood through the cardiovascular system. These heart valves can be rendered less effective by congenital, inflammatory or infectious conditions. Such damage to the valves can result in serious cardiovascular compromise or death. For many years the definitive treatment for such disorders was the surgical repair or replacement of the valve during open heart surgery, but such surgeries are prone to many complications. Because of the drawbacks associated with conventional open-heart surgery, percutaneous and minimally-invasive surgical approaches are garnering intense attention. In one technique, a prosthetic valve is configured to be implanted in a much less invasive procedure by way of catheterization.

In this technique, a prosthetic valve is mounted in a crimped state on the end portion of a flexible catheter and advanced through a blood vessel of the patient until the prosthetic valve reaches the implantation site. The prosthetic valve at the catheter tip is then expanded to its functional size at the site of the defective native valve such as by inflating a balloon on which the prosthetic valve is mounted. For instance, U.S. Pat. Nos. 5,411,522 and 6,730,118, which are incorporated herein by reference, describe collapsible transcatheter heart valves that can be percutaneously introduced in a compressed state on a catheter and expanded in the desired position by balloon inflation or by utilization of a self-expanding frame or stent.

A transcatheter prosthetic heart valve typically has only one functional expanded diameter at which the leaflets of the prosthetic valve can operate as intended. A typical delivery apparatus for a balloon-expandable prosthetic valve can be fluidly connected to a syringe that is used to inject an inflation fluid into a balloon in order to deploy the prosthetic valve at the implantation site. The balloon typically is designed or selected to be inflated with a predetermined amount of fluid that corresponds to a specific volume indicator on the syringe. This allows the user to fill the syringe with the precise amount of fluid required to expand the prosthetic valve to its functional size.

More recently, transcatheter prosthetic heart valves that can be expanded within a range of functional sizes have been developed, such as disclosed in U.S. Patent Application Publication No. 2018/0028310, which is incorporated herein by reference. For the implantation of such prosthetic valves, the physician must be able to select an appropriate volume of the inflation fluid corresponding to a selected prosthetic valve diameter from a range of fill volumes. Using a conventional inflation syringe, it can be difficult for the physician to draw the precise amount of inflation fluid into the syringe that is required to expand a prosthetic valve to a desired size if the required volume does not correspond with one of the volume indicators provided on the syringe.

Accordingly, a need exists for improved devices and methods for accurately measuring the amount of inflation fluid that is needed to expand a prosthetic valve to a selected functional size within a range of functional sizes using an inflation syringe.

SUMMARY

Described herein are embodiments of removable volume indicators that are primarily intended to be used with a syringe for inflating a balloon to expand a prosthetic heart valve, as well as methods for using the same. The volume indicators can be used to draw a precise amount of fluid into the syringe in cases where the required volume does not correspond with any of the existing volume markings on the syringe.

A removable volume indicator can include an indicator body, a window portion extending through a thickness of the indicator body, the indicator body being configured to removably clip onto a syringe. The syringe can have a syringe body and a plunger received in the syringe body, and the window portion of the volume indicator can be configured such that a portion of the syringe plunger in the syringe body is visible through the window portion.

In some embodiments, the volume indicator can further comprise inflation indicia adjacent the window portion. In some embodiments, the inflation indicia can comprise protrusions extending at least partially across the window portion. In other embodiments, the inflation indicia can comprise bands extending across the window portion.

In some embodiments, the indicator body can at least partially opaque. For example, the indicator body can be fully opaque, translucent, or patterned.

In some embodiments, the window portion can be positioned between a first end of the indicator body and a second end of the indicator body and can extend less than the full length of the indicator body.

In a representative embodiment, an assembly comprises a syringe and a volume indicator. The syringe can comprise a syringe body and a plunger, the syringe body having a one or more first engagement elements. The volume indicator can comprise an indicator body and a window portion having inflation indicia along a length thereof; the indicator body comprising one or more second engagement elements configured to engage the first engagement elements.

In some embodiments, the window portion is configured such that a portion of the plunger within the syringe body is visible through the window portion. In some embodiments, the syringe body can comprise volume indicia. In some embodiments, the volume indicia on the indicator body are not aligned with volume indicia on the syringe body when the volume indicator is placed on the syringe. In other embodiments, the syringe body can be blank.

In some embodiments, the volume indicator is configured to removably clip onto the syringe body.

In some embodiments, the one or more first and second engagement elements are arranged on the syringe body and the indicator body such that the volume indicator can be clipped to the syringe in only one orientation.

In some embodiments, the volume indicator can further comprise a gripping portion, (e.g., one or more ridges) configured to allow a user to grip the volume indicator during use. In some embodiments, the syringe can comprise an annular lip at a proximal end portion thereof. The body of the volume indicator can abut the lip such that during use of the syringe to inflate a prosthetic valve, a user can grip the ridges and depress the plunger of the syringe. Depressing the plunger applies a distally directed force to the syringe/volume indicator assembly and requires the user to apply a corresponding proximally directed force to prevent movement of the assembly. The abutment of the volume indicator against the lip during the application of the forces helps restrain the volume indicator against disengaging from the syringe.

In some embodiments, the syringe can further comprise one or more third engagement elements and the volume indicator can further comprise one or more fourth engagement elements configured to engage with the one or more third engagement elements such that the volume indicator is restrained from rotational movement relative to the syringe.

In another representative embodiment, an assembly comprises a syringe and a volume indicator. The syringe can comprise a syringe body and a plunger, the syringe body having a first engagement element. The volume indicator can comprise an indicator body and a window portion having inflation indicia along a length thereof; the indicator body comprising a second engagement element configured to engage the first engagement element. In some embodiments, the first engagement element can be a protrusion extending from an external surface of the syringe. In some embodiments, the second engagement element can be an opening configured to engage the protrusion. The syringe body can further comprise a third engagement element and the volume indicator can further comprise a fourth engagement element configured to engage the third retaining element to restrain the volume indicator from rotational motion relative to the syringe body.

In another representative embodiment, a method for using a volume indicator with a syringe can comprise placing a volume indicator on a syringe, the syringe comprising a syringe body and a plunger received in the syringe body and the volume indicator comprising an indicator body and volume indicia on the indicator body; filling the syringe body with an amount of fluid corresponding to one of the volume indicia on the indicator body; and fluidly connecting the syringe to a delivery apparatus for a prosthetic valve.

In some embodiments, the act of placing the volume indicator on the syringe can comprise engaging one or more first engagement elements on the syringe body with one or more second engagement elements on the indicator body.

In some embodiments, the method can further comprise inserting into a body of a patient a distal end portion of the delivery apparatus and a prosthetic heart valve mounted in a radially compressed configuration on a balloon mounted on a distal end portion of the delivery apparatus.

In some embodiments, the method can further comprise advancing the distal end portion of the delivery apparatus and the radially compressed prosthetic valve through the patient's vasculature to position the prosthetic valve at a selected implantation area and actuating the plunger of the syringe to inject the fluid into the balloon, thereby inflating the balloon and radially expanding the prosthetic heart valve.

In some embodiments, the prosthetic heart valve can be expanded to an expanded functional diameter within a range of expanded diameters, and the act of filling the syringe body comprises selecting a fill volume needed to expand the prosthetic heart valve to a selected expanded diameter within the range of expanded diameters.

In some embodiments, the volume indicia on the indicator body are not aligned with volume indicia on the syringe body when the volume indicator is placed on the syringe.

In some embodiments, the volume indicator is selected from a kit of volume indicators. In some embodiments, each volume indicator in the kit corresponds to a different nominal valve size. In some embodiments, the kit comprises a first volume indicator corresponding to a prosthetic heart valve having a nominal size of 20 mm, a second volume indicator corresponding to a prosthetic heart valve having a nominal size of 23 mm, a third volume indicator corresponding to a prosthetic heart valve having a nominal size of 26 mm, and a fourth volume indicator corresponding to a prosthetic heart valve having a nominal size of 29 mm.

In another representative embodiment, an assembly comprises a removable volume indicator for mounting on a syringe, the volume indicator comprising an indicator body and inflation indicia spaced along a length thereof; and a delivery apparatus for implanting a prosthetic heart valve, the apparatus comprising a balloon mounted on a distal portion thereof.

In some embodiments, the assembly can further comprise a prosthetic heart valve that is expandable to an expanded functional diameter within a range of expanded diameters, wherein the inflation indicia correspond to expanded diameters of the range.

In another representative embodiment, a kit can comprise at least first and second removable volume indicators for mounting on the same syringe, each volume indicator comprising an indicator body and inflation indicia spaced along a length thereof, the inflation indicia of the first volume indicator corresponding to a range of expanded diameters of a first prosthetic valve and the inflation indicia of the second volume indicator corresponding to a range of expanded diameters of a second prosthetic valve that is larger than the first prosthetic valve. In some embodiments, the kit can further comprise a third volume indicator, and a fourth volume indicator.

In some embodiments, the kit can further comprise a delivery apparatus that can be used to implant the first prosthetic heart valve and the second prosthetic heart valve, the apparatus comprising a balloon mounted on a distal portion thereof. In some embodiments, the kit can further comprise a first prosthetic heart valve and/or a second prosthetic heart valve.

The various innovations of this disclosure can be used in combination or separately. This summary is provided to introduce a selection of concepts in a simplified form that a further described below in the detailed description. This summary is not intended to identify key features or essential features of the claimed subject matter. The foregoing and other objects, features, and advantages of the disclosure will become more apparent from the following detailed description, which proceeds with reference to the accompanying figures.

DETAILED DESCRIPTION

In particular embodiments, a delivery assembly for implanting a prosthetic, transcatheter heart valve via a patient's vasculature includes a syringe for inflating a balloon of a delivery apparatus for the purpose of radially expanding a prosthetic valve radially crimped on the balloon. The balloon can be mounted on a distal end portion of a shaft of the delivery apparatus. The balloon and the crimped prosthetic valve can be inserted into the vasculature of a patient via an introducer sheath and, once the balloon and the crimped prosthetic valve reach a suitable location in the body, the prosthetic valve can be expanded at the treatment site (e.g., the native aortic valve).

Figure 1:
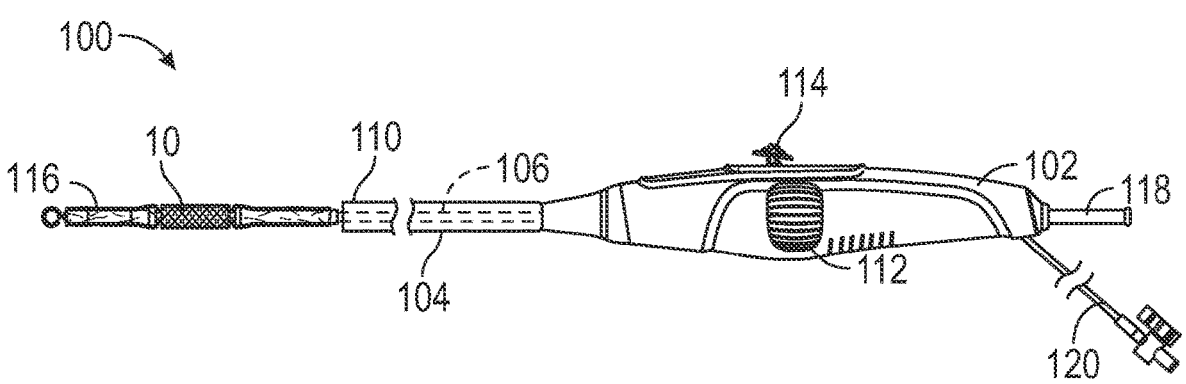
FIG. 1 is a side elevation view of a representative embodiment of a delivery apparatus for implanting a prosthetic heart valve.

FIG. 1 shows a delivery apparatus 100, according to one embodiment, adapted to deliver a prosthetic heart valve, such as the illustrated prosthetic heart valve 10. The prosthetic heart valve 10 can be, for example, a prosthetic aortic valve that is adapted to be implanted in the native aortic valve, although in other embodiments the prosthetic valve 10 can be implanted in any of the other native valves of the heart (the native mitral, tricuspid, or pulmonary valves). The delivery apparatus 100 generally includes a handle 102, a first elongated shaft 104 extending distally from the handle 102, and a second elongated shaft 106 extending distally from the handle 102 and co-axially through the first shaft 104.

In some embodiments, the first shaft 104 can be configured as a steerable guide catheter having an adjustable curvature for use in steering the delivery apparatus through the patient's vasculature. For example, the first shaft 104 can include a steerable distal section 110, the curvature of which can be adjusted by the operator to assist in guiding the apparatus through the patient's vasculature. A steering or pull wire (not shown) can extend through the shaft 104 and can have a distal end fixed at a location along the distal section 110 and a proximal end operatively connected to an adjustment mechanism, such as the illustrated knob 112, on the handle 102.

In some embodiments, the first shaft 104 and the second shaft 106 can be moved relative to each other (axially and/or rotationally) to facilitate delivery and positioning of the prosthetic valve 10 at an implantation site in the patient's body. The handle 102 can include an adjustment mechanism to produce relative movement between the shafts 104, 106. For example, the handle can include a slidable adjustment knob 114 that is operatively connected to the second shaft 106 and configured to produce axial movement of the second shaft 106 in the proximal and distal directions relative to the first shaft 104.

An inflatable balloon 116 can be mounted along the distal end portion of the second shaft 106, which can be referred to as a balloon catheter. As depicted in FIG. 1, the prosthetic valve 10 can be radially crimped around the balloon 116 for delivery into a patient's vasculature. Once the prosthetic valve 10 reaches the desired implantation site (e.g., within the native aortic valve), the balloon can be inflated to radially expand the prosthetic valve against the surrounding tissue.

The delivery apparatus 100 can include a proximal port 118 extending from the handle 102. The proximal port 118 is in fluid communication with a longitudinally extending fluid passageway of the delivery apparatus for delivering an inflation fluid to the balloon 116. The handle 102 can further include a side arm 120 which can be, for example, a flush tube having an internal passage that fluidly communicates with a lumen defined by the handle 102. The flush tube can terminate at or adjacent to a seal member where the flush tube connects with an inner passage defined by the shaft 106 and/or the shaft 104.

The proximal port 118 can be formed with a fluid passageway that is fluidly connectable to a fluid source (e.g., a syringe filled with saline, see FIG. 3) to inflate the balloon 116 and optionally flush the space between the inner and outer balloon catheter shafts. Thus, the fluid passageway of the proximal port 118 can be in fluid connection with an annular space between the first and second shafts such that fluid from the fluid source can flow through the fluid passageway, through the space between the shafts, and into the balloon 116 to inflate the same and deploy the prosthetic valve 10. In alternative embodiments, the proximal port 118 can be in communication with a lumen of the second shaft 106, which serves as a fluid passageway for delivering an inflation fluid from the fluid source to the balloon 116.

In some embodiments, the proximal port 118 can further comprise a stopcock (not shown) movable between an open position and a closed position (e.g., by manual actuation by a physician). Wherein when the stopcock is in the open position fluid from the fluid source can flow into the fluid passageway, and wherein when the stopcock is in the closed position fluid from the fluid source is prevented from flowing into the fluid passageway.

The first and second shafts 104, 106 can be formed from any of various suitable materials, such as nylon, braided stainless steel wires, or a polyether block amide (commercially available as Pebax®), to name a few. The shafts can have longitudinal sections formed from different materials in order to vary the flexibility of the shafts along their lengths. The second shaft 106 can have an inner liner or layer formed of Teflon® to minimize sliding friction with a guide wire.

Further details regarding the delivery apparatus 100 and methods for delivering and deploying a prosthetic valve using the delivery apparatus can be found, for example, in U.S. Publication No. 2017/0065415, which is incorporated herein by reference. Other examples of delivery apparatuses that can be used to implant a prosthetic heart valve with devices disclosed herein are described in U.S. Pat. Nos. 8,568,472 and 9,061,119, which are incorporated herein by reference.

Figure 2:
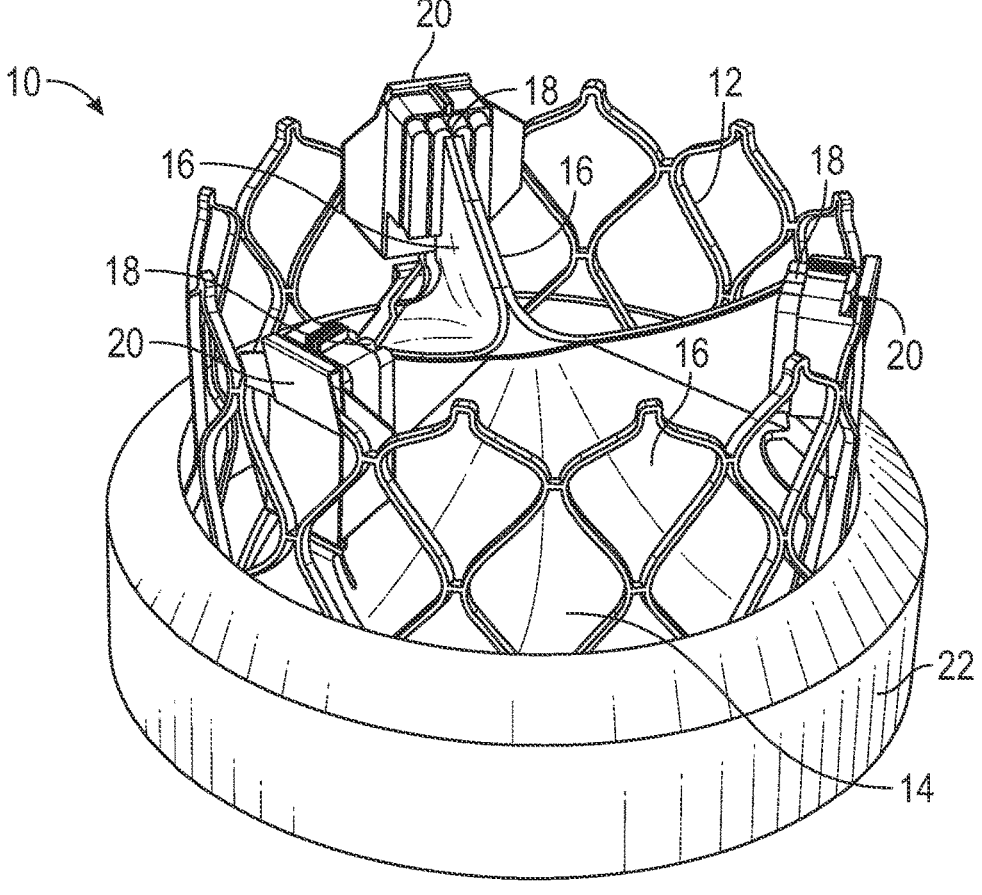
FIG. 2 is a perspective view of a representative embodiment of a prosthetic heart valve.

Referring to FIG. 2, the prosthetic heart valve 10 comprises a stent or frame 12 and a valvular structure 14 supported by the frame and configured to regulate the flow of blood through the prosthetic valve. In some embodiments, the prosthetic valve 10 is adapted to be implanted in the native aortic valve and can be implanted in the body using, for example, the delivery apparatus 100 described above. The frame 12 can comprise a plastically expandable material, such as stainless steel, a nickel based alloy (e.g., a nickel-cobalt-chromium alloy), polymers, or combinations thereof, so that the frame 12 plastically expands when the prosthetic valve expands from the crimped, radially compressed configuration (FIG. 1) to the radially expanded configuration (FIG. 2) upon inflation of the balloon 116.

The valvular structure 14 can comprises a plurality of leaflets 16 mounted inside of the frame. The opposing sides of each leaflet 16 can be paired with adjacent leaflets to form commissures 18 of the valvular structure. The commissures 18 can be mounted to the frame via reinforcing members 20. The prosthetic valve 10 can also include a sealing member 22 mounted on the outside of the frame. The sealing member 22 is configured to help seal the prosthetic valve against surrounding tissue and prevent or minimize perivalvular leakage. The leaflets 16 can be made from any of various suitable biocompatible materials, including natural tissue, such as bovine pericardial tissue (or pericardial tissue from other sources) or synthetic materials, such as any of various fabrics or non-fabric materials (e.g., polyurethane). The reinforcing members 20 and the sealing member 22 desirably are made of a fabric material, such as polyethylene terephthalate (PET) fabric, although non-fabric materials and natural tissue also could be used. Further details of the prosthetic valve 10 are disclosed in U.S. Patent Application Publication No. 2018/0028310, which is incorporated herein by reference. Other types of prosthetic heart valves that can deployed using any of the devices and methods disclosed herein are described in U.S. Pat. Nos. 7,510,575; 7,993,394; and 9,393,110, which are incorporated herein by reference.

In particular embodiments, the prosthetic valve 10 can be radially expanded to an expanded state having an outer diameter within a range of expanded diameters. This allows the physician to expand the prosthetic valve 10 to a size that closely corresponds the diameter of the native annulus in which the prosthetic valve is to be implanted. For example, in one specific implementation, a prosthetic valve 10 having a "nominal" size of 23 mm can be expanded to a diameter within a range of diameters from about 21.5 mm to about 23.3 mm. As used herein, the "nominal" size of a prosthetic valve is an approximate value corresponding to the outer diameter of the prosthetic valve in the expanded state. The size range of expanded diameters for a prosthetic valve typically includes the nominal size of the prosthetic value. Typically, although not necessarily, the nominal size of a prosthetic valve defines the upper limit of the size range of expanded diameters or is close to the upper limit of the size range.

Figure 3:
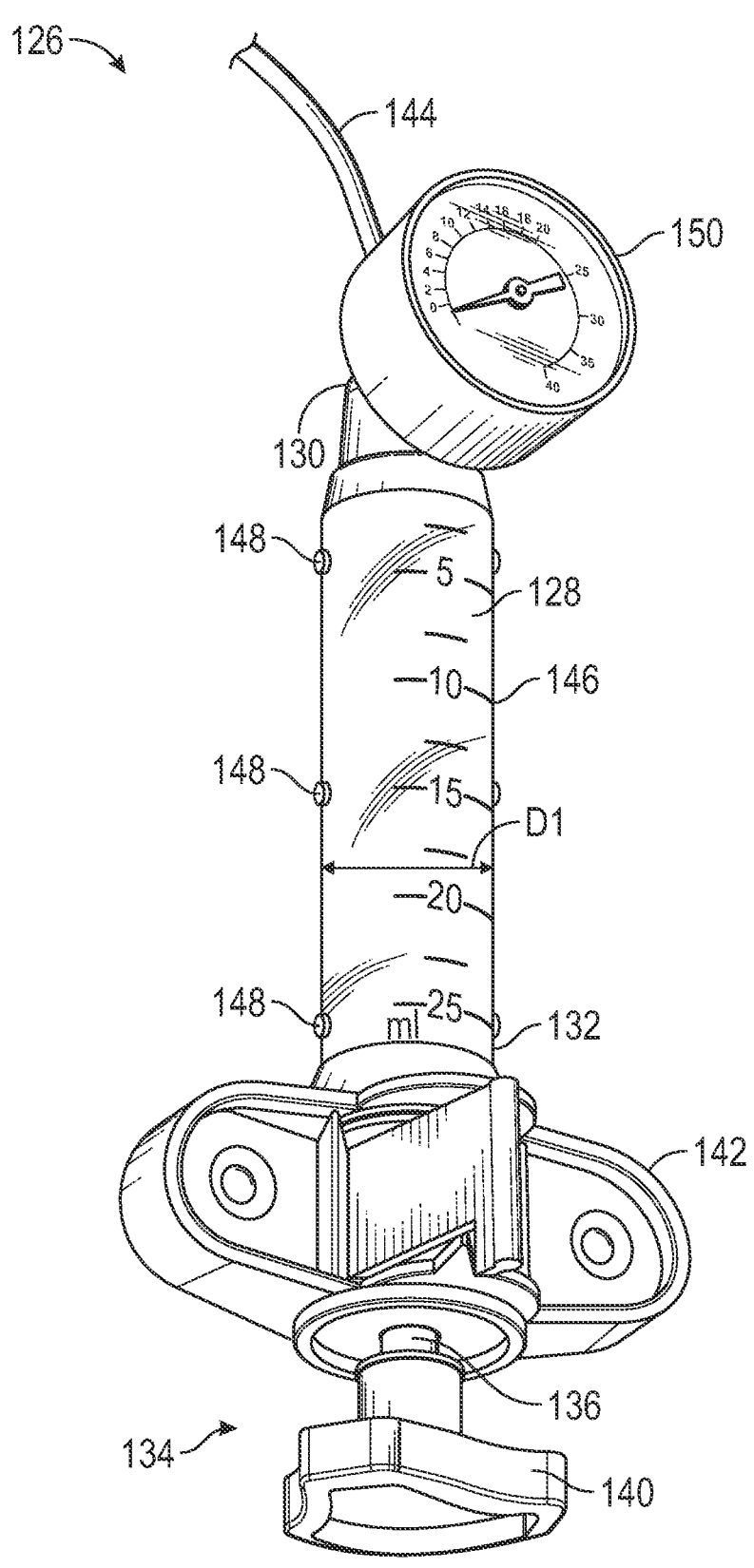
FIG. 3 is a perspective view of a representative embodiment of a syringe that can be used to inflate the balloon of a delivery apparatus, according to one embodiment.

Once the prosthetic heart valve 10 has been positioned at the desired implantation location, the physician can introduce an appropriate amount of the inflation fluid into the balloon 116 to radially expand the prosthetic valve to a desired diameter at which the prosthetic valve securely engages the annulus of the native heart valve without over-expanding the native annulus. FIG. 3 shows one example of a syringe 126 that can be used to inject the inflation fluid into the balloon 116. In some implementations, the final diameter of the prosthetic valve 10 can be predetermined by measuring the native annulus using known techniques. In other implementations, the final diameter of the prosthetic valve can be determined during the implantation procedure, for example, as the prosthetic valve is being expanded. The syringe 126 can be equipped with a volume indicator 200 (FIGS. 4A-4C) that allows the physician to more accurately select or measure a volume of fluid needed to expand the prosthetic valve to the desired, final diameter, as further described below.

Referring to FIG. 3, in the illustrated embodiment, the syringe 126 can have a cylindrical syringe body 128 having an interior chamber for containing the inflation fluid. The syringe body 128 has a diameter $D_1$, a first end 130, and a second end 132. The syringe 126 can include a conduit 144 (e.g., medical grade flexible polymeric tubing) that extends from the first end 130 of the body 128. The first end 130 of the body 128 can be formed with an opening that fluidly connects the interior chamber of the body 128 with the adjacent end of the conduit 144. Prior to introducing the delivery apparatus 100 into the patient's body, the opposite end of the conduit 144 (not shown) can be fluidly connected to the proximal port 118 of the delivery apparatus. For example, the conduit 144 can be connected to the proximal port 118 using a rotating Luer connector.

The syringe 126 can further comprise a plunger 134 comprising a shaft 136 that extends into the interior chamber of the body 128, a plunger head 138 (FIG. 8) attached to one end of the shaft 136 and located within the interior chamber of the body 128, and a plunger handle 140 attached to the other end of the shaft 136. The second end 132 of the body 128 can have an opening through which the shaft 136 of the plunger 134 extends. A pressure gauge 150 can be mounted on the syringe body 128 and can be used to measure the pressure of the inflation fluid as the fluid is being ejected from the syringe and into the delivery apparatus.

A syringe gripping portion 142 can be mounted against the second end 132 of the body and can include a central opening through the plunger shaft 136 extends. Thus, in use, the physician can grip the syringe gripping portion 142 with one hand and grip the handle 140 of the plunger 134 with the other hand in order to adjust the position of the plunger head 138 within the body 128. The physician can fill the syringe body with a desired amount of the inflation fluid by pulling the plunger 134 away from the syringe body 128, which draws the fluid into the interior chamber of the body (assuming the conduit 144 is fluidly connected to another source of the inflation fluid). Alternatively, the inflation fluid can be introduced into the syringe body by completely removing the plunger 134 form the syringe body 128 so that the inflation fluid can be poured through the opening at the second end 132 of the body. The physician can push fluid out of the syringe body 128 by pushing the plunger 134 further into the interior chamber of the syringe body.

The syringe body 128 can be transparent or at least translucent to allow a user to see the amount of the inflation fluid and the position of the plunger head 138 inside the body. In some embodiments, the external surface of the syringe body can comprise a series of markings or measurement indicia 146 that allows the user to measure the amount of inflation fluid within the body 128. In other embodiments, the syringe can lack measurement indicia altogether (e.g., it can be a blank syringe). As shown in FIG. 3, in the illustrated embodiment, the measurement indicia 146 are arranged with the volume marking corresponding to the smallest value adjacent the first end 130 of the body 128 (which is the outlet of the syringe body) and the volume marking corresponding to the largest value adjacent the second end 132 of the body. In this manner, as the user draws fluid from a source into the syringe body 128 via the conduit 144 by pulling the plunger handle 140, the user can draw a predetermined amount of fluid into the syringe body 128 by aligning the plunger head 138 with the volume marking corresponding to the desired amount of fluid.

The syringe body 128 can further comprise one or more first engagement elements 148 projecting outwardly from the external surface of the body. Each engagement element 148 can be a small cylindrical projection as shown, although the engagement elements can have any of various other shapes in cross-section (e.g., square, rectangle, triangle, ellipse, and/or combinations thereof) in other embodiments. In some embodiments, the one or more first engagement elements 148 can comprise a plurality of first engagement elements that can be spaced apart from each other along a length of the syringe body 128. In other embodiments, the one or more first engagement elements 148 can be a single engagement element. In particular embodiments, the single first engagement element 148 may be located at the first end portion 130 of the syringe and may extend outward from a surface thereof (e.g., the upward facing surface in the orientation shown in FIG. 9).

In particular embodiments, the syringe 126 comprises a model QL38 syringe available from Atrion Medical (Arab, AL) that is modified to include one or more first engagement elements 148 on the syringe body.

Known delivery systems typically are provided with a prosthetic valve that has only one functional expanded diameter that is expanded using a balloon that is inflated with a predetermined amount of fluid that corresponds to one of the volume indicators 146 on the syringe body 128 (usually the volume of fluid is whole number). This allows the user to fill the syringe with the precise amount of fluid required for the procedure. However, if the prosthetic valve has more than one functional expanded diameter and instead can be expanded within a range of expanded diameters, it can be difficult for the user to draw the precise amount of inflation fluid into the syringe body that is required to expand a prosthetic valve to a desired size if the required volume falls between two of the volume markings 146.

Figure 4C:
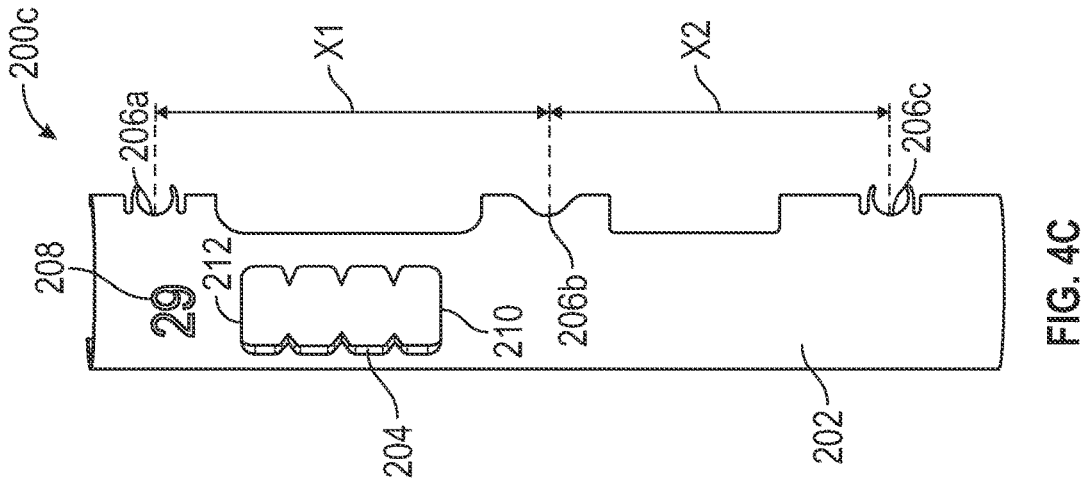
FIG. 4A-4C are front elevation views of three different volume indicators that can be mounted on a syringe.
Figure 4B:
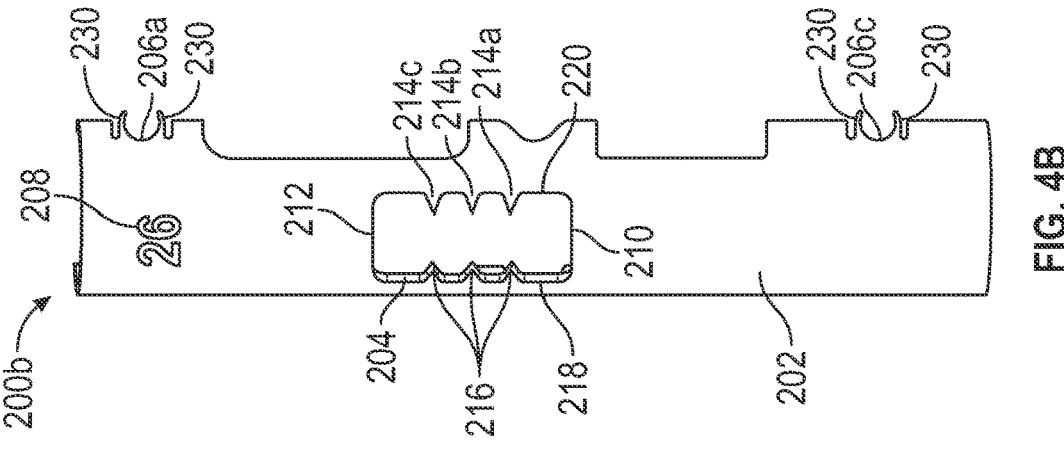
Figure 4A:
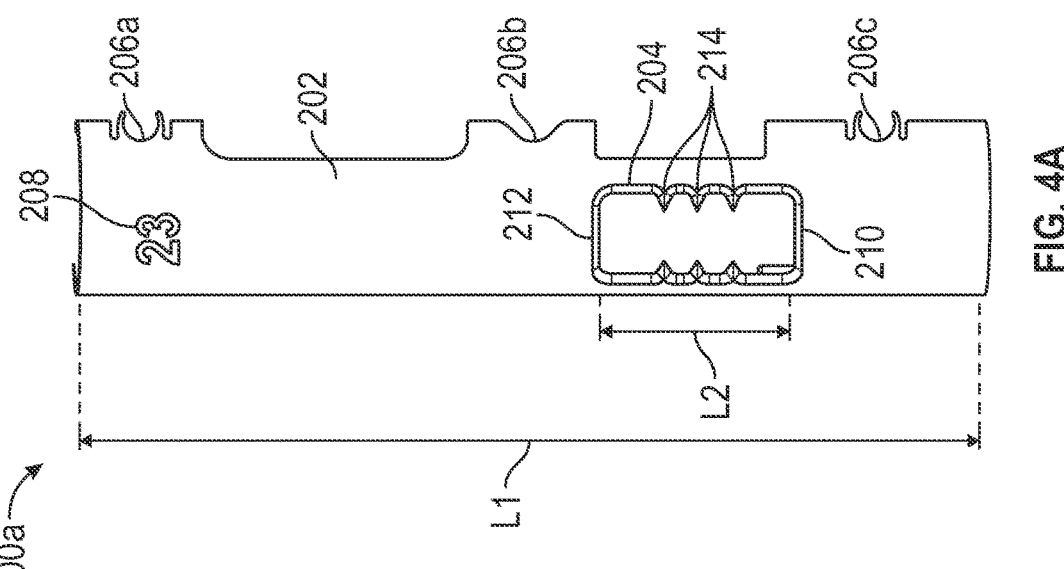

FIGS. 4A-4C illustrate a representative embodiment of a set of removable volume indicators 200a, 200b, 200c for use with a syringe, such as the syringe 126. The removable volume indicators can be used to draw a precise amount of fluid into the syringe in cases where the required volume does not correspond with any of the existing volume markings on the syringe. For ease of description, the reference number 200 is used when describing features common to each volume indicator 200a, 200b, 200c. Each volume indicator 200 can comprise an indicator body 202 having a window portion 204 formed within the indicator body. In some embodiments, the volume indicator can further comprise one or more second engagement elements 206 that can mate with one or more corresponding first engagement elements 148 on the syringe body 128.

As shown in FIGS. 4A-4C, each volume indicator 200 can correspond to a nominal prosthetic valve size. In some embodiments, a single volume indicator may be packaged and/or sold with a correspondingly sized prosthetic valve and/or a suitable delivery apparatus. In other embodiments, two or more volume indicators can form an assembly or kit and the volume indicators of the kit can be packaged together for delivery to the end user. In some embodiments, the kit can further comprise a delivery apparatus, a prosthetic valve, a syringe, and/or any combination of these elements. An exemplary kit can comprise two or more volume indicators 200, a delivery apparatus 100, and a prosthetic valve 10. Alternatively, the prosthetic valve 10 can be packaged and sold separately from the kit including two more volume indicators and a delivery apparatus. The kit can include a number of volume indicators that equals the number of different nominal valve sizes that can be used with the same delivery apparatus. Another exemplary assembly can comprise three volume indicators 200 and a delivery apparatus 100. Yet another exemplary assembly can comprise two or more volume indicators 200 and a syringe 126.

During an implantation procedure, a physician can have access to multiple volume indicators 200, for example, in a kit, and select the appropriate volume indicator corresponding to the appropriately sized prosthetic valve. The variety of volume indicators allow a single syringe 126 to be used for the implantation procedure regardless of the size of prosthetic valve 10 ultimately selected by the physician. Each volume indicator 200 can be labeled, marked, colored, and/or patterned to indicate a corresponding nominal prosthetic heart valve size. In the illustrated embodiment, each volume indicator has a molded embossment 208 indicating the nominal diameter of the corresponding prosthetic valve. In other embodiments, the volume indicator 200 can be labelled using, for example, pad-printing, laser engraving, or other method of marking.

Referring now to FIG. 4A, the indicator body 202 can have a length $L_1$ and can be sized to cover at least a portion of the measurement indicia 146 of the syringe body 128 (when such measurement indicia are present) when the volume indicator 200 is placed on the syringe 126. In particular embodiments, the body 202 extends the entire length of the syringe body 128 or substantially the entire length of the syringe body 128, and covers all of the measurement indicia 146 on the syringe body 128. In some embodiments, the indicator body 202 can be opaque or substantially opaque such that the measurement indicia 146 of the syringe 126 are completely obscured, partially obscured, or otherwise minimized. Thus, the volume indicator 200 helps prevent a physician from confusing the measurement indicia 146 on the syringe body 128 with the volumes indicated by the volume indicator 200 itself. In other embodiments, wherein the volume indicator is used with a blank syringe, the volume indicator can be opaque, transparent, substantially transparent, or translucent.

Figure 5:
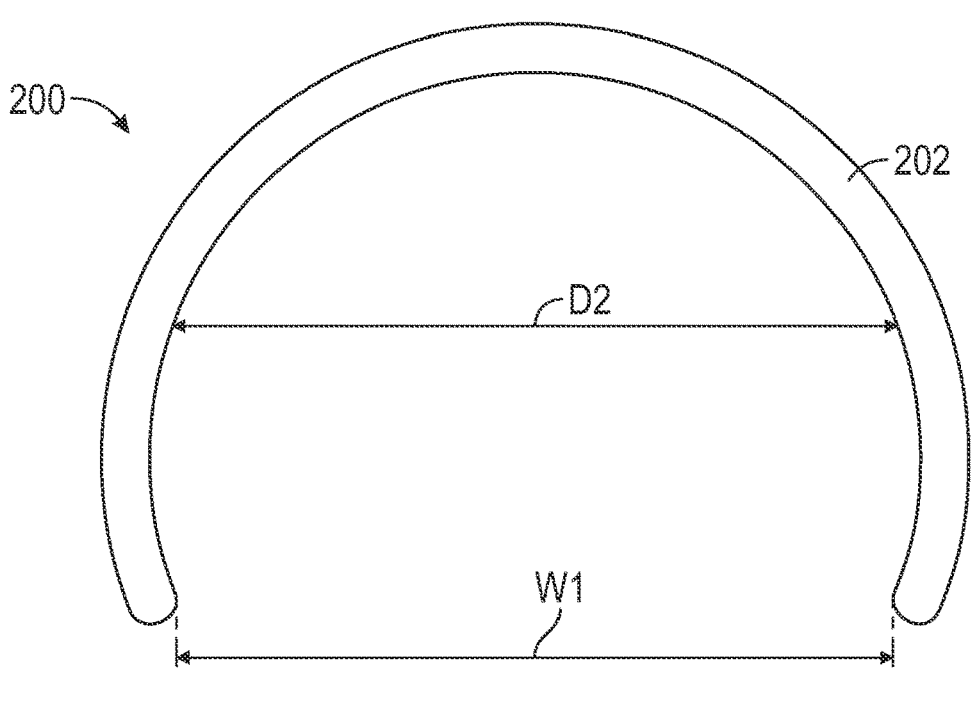
FIG. 5 is an end view of the volume indicator of FIG. 4A.

As shown in FIG. 5, the indicator body 202 can have a C-shaped cross-section having an opening of width $W_1$ such that it can removably clip or "snap" onto the syringe body 128. The width $W_1$ of the opening can be slightly smaller than the diameter $D_1$ of the syringe body 128 such that the body 202 deforms or expands slightly to allow the syringe body 128 to pass through the opening. The width $W_1$ of the opening can help retain the syringe body 128 within the volume indicator 200. In particular embodiments, the indicator body 202 can have an inner diameter $D_2$ that is the same as or slightly smaller than the outer diameter $D_1$ of the syringe body so that the indicator body 202 forms a tight or snug fit against the outer surface of the syringe body 128.

Referring again to FIGS. 4A-4C, in some embodiments, the one or more second engagement elements 206 (e.g., three in the embodiment shown in FIGS. 4A-4C) can be configured to mate with corresponding first engagement elements 148 extending from the syringe body 128 (see e.g., FIG. 3). As shown in the illustrated embodiment, the one or more second engagement elements 206 can be C-shaped notches formed along an edge of the indicator body 202 and shaped to receive the one or more first engagement elements 148. Additionally, one or more of the engagement elements 206 can be configured to form releasable connections with corresponding first engagement elements.

For example, as shown in FIG. 4B, second engagement elements 206a and 206c can be configured to form a snap-fit connection with corresponding first engagement elements 148, while second engagement element 206b can be shaped to mate with a corresponding first engagement elements 148 but does not to form a snap-fit or other type of secure connection with the corresponding first engagement element 148. Each second engagement element 206a, 206c can comprise two arcuate, deflectable arms 230 that are configured to be placed around a corresponding first engagement element 148. The arms 230 are sized and shaped to deflect away from each other as a corresponding first engagement element 148 is inserted between the free ends of the arms and then revert back to their original shape when the first engagement element 148 is located entirely between the arms. The snap-fit connections help secure the volume indicator 200 against the syringe body 128 and prevents movement of the volume indicator relative to the syringe body. It should be noted that all of the second engagement elements or only one of the second engagement elements can be configured to form a snap-fit connection with corresponding first engagement elements in alternative embodiments.

It also should be noted that, while in the illustrated embodiment the second engagement elements 206 are C-shaped notches configured to receive correspondingly shaped cylindrical first engagement elements 148, in other embodiments, the second engagement elements 206 can be any of various sizes and shapes (e.g., circular, rectangular, oval, etc.) configured to mate with the first engagement elements 148.

Moreover, in alternative embodiments, one or more of the second engagement elements 206 can be openings formed in the indicator body 202 that are configured to form releasable connections with respective first engagement elements 148 (e.g., by snapping, clipping, or inserting the first engagement elements into or through the second engagement elements). Examples of such embodiments are described in more detail below with reference to FIGS. 9-10.

Referring to FIG. 4C, in some embodiments, the one or more second engagement elements 206 can be spaced apart from each other along a length of the indicator body 202. In some embodiments, two or more of the one or more second engagement elements 206 can be disposed collinearly with one another. The distance between adjacent engagement elements 206 can vary such that the volume indicator 200 can only be connected to the syringe body 128 in one orientation, preventing mismeasurement by incorrect mounting of the volume indicator on the syringe body. For example, in the illustrated embodiment, second engagement elements 206a and 206b are spaced apart a first distance $X_1$ and second engagement elements 206b and 206c are spaced apart a second distance $X_2$. The first and second distances $X_1$ and $X_2$ can differ from one another. For example, $X_1$ can be greater than $X_2$, as depicted in FIG. 4C. The first engagement elements 148 on the syringe body 128 can be correspondingly spaced. In the illustrated embodiment, the engagement elements 148, 206 are spaced from each other such that the volume indicator 200 can only be placed on the syringe body 128 with the size indicator 208 oriented at the second end portion 132 of the syringe body.

The window portion 204 can be formed within the indicator body 202 and can extend a length $L_2$, wherein $L_2$ is less than the length of the indicator body $L_1$. Referring again to FIG. 4A, in some embodiments, the length $L_2$ can be less than the majority of the length $L_1$ of the indicator body (i.e., less than 50% of the length $L_1$). As such, the window portion 204 in the illustrated embodiment (which includes inflation indicia 214, discussed below) is used to measure a specific range of volumes that is much less than the total volume capacity of the syringe. However, in alternative embodiments, the window portion 204 (and the corresponding indicia 214) can extend a length $L_2$ that is greater 50% of the length $L_1$ or substantially equal to the length $L_1$. The window portion can have a first end 210 configured to be disposed closer to the first end portion 130 of the syringe body 128 when the volume indicator is placed on the syringe body and a second end 212 configured to be disposed closer to the second end portion 132 of the syringe body 128 when the volume indicator is placed on the syringe body.

In some embodiments, as shown in FIGS. 4-10, the window portion 204 can be an opening or aperture extending completely through the indicator body 202 such that a portion of the plunger 134 (e.g., the head 138) is visible through the window portion. In other embodiments, the window portion 204 can be a portion of the body 202 formed of transparent, semi-transparent, or translucent material configured such that a portion of the plunger 134 is visible through the window.

The window portion 204 can further comprise inflation indicia 214 corresponding to the volume of fluid necessary to expand the prosthetic heart valve to a selected diameter within the range of diameters for a particular prosthetic valve. The inflation indicia 214 can be a series of markings or protrusions that visually indicate to a physician the volumes of fluid that are needed to expand the prosthetic heart valve to different diameters. In a volume indicator 200a for use with a prosthetic valve having a nominal diameter of 23 mm, the inflation indicia can, for example, correspond to the volume of fluid necessary to expand the valve to diameters of 22.5 mm, 23 mm, and 23.5 mm, respectively. In a volume indicator 200b for use with a prosthetic valve having a nominal diameter of 26 mm, the inflation indicia can, for example, correspond to the volume of fluid necessary to expand the valve to diameters of 24.5 mm, 25.8 mm, and 27 mm, respectively. In a volume indicator 200c for use with a prosthetic valve having a nominal diameter of 29 mm, the inflation indicia can, for example, correspond to the volume of fluid necessary to expand the valve to diameters of 27.5 mm, 28.8 mm, and 30.0 mm, respectively. In an exemplary volume indicator for use with a prosthetic valve having a nominal diameter of 21 mm, the inflation indicia can, for example, correspond to the volume of fluid necessary to expand the valve to diameters of 20.5 mm, 21 mm, and 21.5 mm, respectively.

As shown in FIGS. 4A-4C, the window portion 204 of each indicator 200a, 200b, 200c can be located at a different position along the length of the indicator body 202 depending on the nominal size and diameter range of the corresponding prosthetic valve. The location of the window portion can correspond with a range of syringe volumes used to expand each different nominally sized prosthetic valve to a corresponding range of diameters. This variability between volume indicators 200 allows the same syringe 126 to be used with each volume indicator and therefore with each prosthetic valve. In other embodiments, the window portion 204 can be located at the same position for each volume indicator 200, and the inflation indicia 214 can be located at a different position along the length of the window 204 depending on the nominal size and diameter range of the corresponding prosthetic valve. The location of the volume indicia 214 within the window portion 204 can correspond with a range of syringe volumes used to expand each different nominally sized prosthetic valve corresponding to a range of diameters.

Referring now to FIG. 4B, in the illustrated embodiment, the inflation indicia 214 are triangular protrusions 216 extending inwardly from both sides 218, 220 of the window portion 204. Each protrusion can extend partially across the width of the window portion as shown. In other embodiments, the inflation indicia can extend across the entire width of the window portion 204; in other words, the indicia can comprise a plurality of bands spaced along the length of the window portion with each band extending from one side 218 to the other side 220 of the window portion. In still other embodiments, the inflation indicia can be notches in the sides 218, 220 of the window portion. The inflation indicia 214 can be marked (e.g., numbered), colored, and/or patterned to denote the prosthetic heart valve diameter that corresponds with each indicator such that a physician can quickly and easily assess whether the correct volume of fluid is contained within the syringe body.

In some embodiments, the inflation indicia can be made of metal, plastic and/or other material. In some embodiments, the inflation indicia can be formed integrally with the window portion. Alternatively, the inflation indicia can be formed separately and be joined later in the fabrication process, such as by welding, adhesive, and/or mechanical means such as screws. In embodiments wherein the window portion is a transparent portion of the indicator body, the inflation indicia can be colored and/or patterned, transparent or semi-transparent bands formed integrally with the window portion.

In some embodiments, the inflation indicia can include markings that communicate valve-specific information (e.g., the volume of fluid within the syringe or the deployed valve diameter for each indicator mark). These markings can be created using, for example, molded embossments, pad-printing, laser engraving, or other method of marking.

In one specific embodiment, the inflation indicia 214 can indicate increasingly larger diameter sizes sequentially from the first end 210 of the window to the second end 212. For example, referring now to FIG. 7, a volume indicator 200 for use with a valve having a nominal diameter of 23 mm can have a first inflation indicator 214a corresponding to a diameter of 21.5 mm, a second inflation indicator 214b corresponding to a diameter of 22.7 mm, and a third inflation indicator 214c corresponding to a diameter of 23.3 mm.

Figure 7:
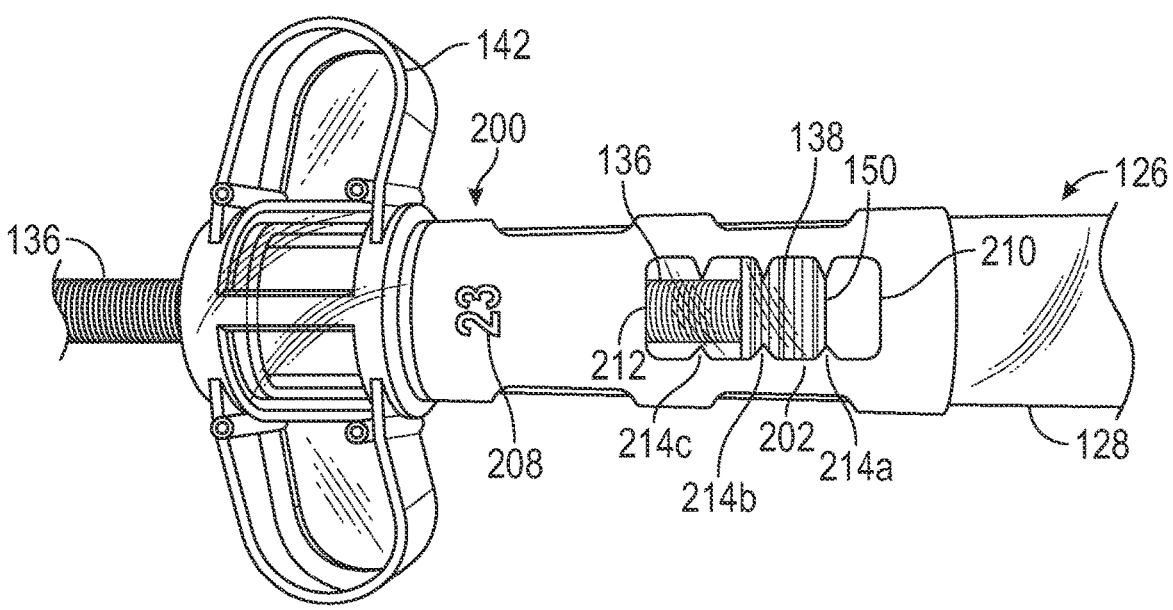
FIG. 7 is a perspective view of an embodiment of a volume indicator disposed on the syringe of FIG. 3.

In use, when the volume indicator 200 of FIG. 7 is placed on a syringe, a physician may fill the syringe (e.g., by pulling plunger 134 while the conduit 144 is connected to a fluid source) until, for example, the end surface 150 of plunger head 138 of the plunger 134 aligns with the inflation indicator 214 corresponding to a selected diameter size. In other embodiments, the syringe may be filled by aligning an O-ring on the plunger head 138 with the inflation indicator 214 corresponding to a selected diameter size. Thusly aligned, the syringe body contains the necessary volume of fluid to expand the prosthetic valve 10 to the selected diameter size. For example, to expand the prosthetic valve to a diameter of 22.7 mm, the physician can fill the syringe until the plunger head 138 of the plunger 134 is aligned with the second inflation indicator 214b. The prosthetic valve can then be expanded, as explained in more detail below. It should be noted that any portion of the plunger head 138 can be used to measure the amount of fluid needed to expand the prosthetic valve to a selected size, so long as the volume indicia 214 are positioned at locations that provide the required volume for expansion when aligned with the portion of the plunger head 138 that is used for measuring the amount of fluid.

In another embodiment, the inflation indicia on a volume indicator can indicate or correspond to increasingly larger diameter sizes sequentially from the second end 212 of the window 204 to the first end 210. Assuming the entire syringe body is filled with the inflation fluid, each indicator can correspond to a volume of fluid that would be ejected from the syringe body starting from the second end 132 of the syringe 126 for expanding the prosthetic valve to a selected diameter. For example, referring to FIG. 8, a volume indicator for use with a prosthetic valve having a nominal diameter of 23 mm can have a first inflation indicator 222a corresponding to a diameter of 21.5 mm, a second inflation indicator 222b corresponding to a diameter of 22.7 mm, and a third inflation indicator 222c corresponding to a diameter of 23.3 mm.

In some embodiments (see e.g., FIG. 9), the body 202 of the volume indicator 200 can further comprise a gripping portion, for example, a plurality of spaced ridges 226, configured to enhance a user's grip on the volume indicator 200 during use. The syringe can comprise an annular lip 156 at the second end portion 132 of the syringe body 128. The body 202 of the volume indicator 200 can have a length $L_1$ such that a proximal end portion 228 of the volume indicator 200 abuts the lip 156. During use of the syringe to inflate a prosthetic valve, a user can grip the ridges 226 of the volume indicator 200 and depress the plunger 136 of the syringe 126. Depressing the plunger 136 applies a distally directed force to the syringe/volume indicator assembly and requires the user to apply a corresponding proximally directed force to prevent movement of the assembly. The abutment of the proximal end portion 228 of the volume indicator 200 against the lip 156 of the syringe 126 during the application of the proximally and distally directed forces helps restrain the volume indicator 200 against disengaging from the syringe 126.

Figure 8:
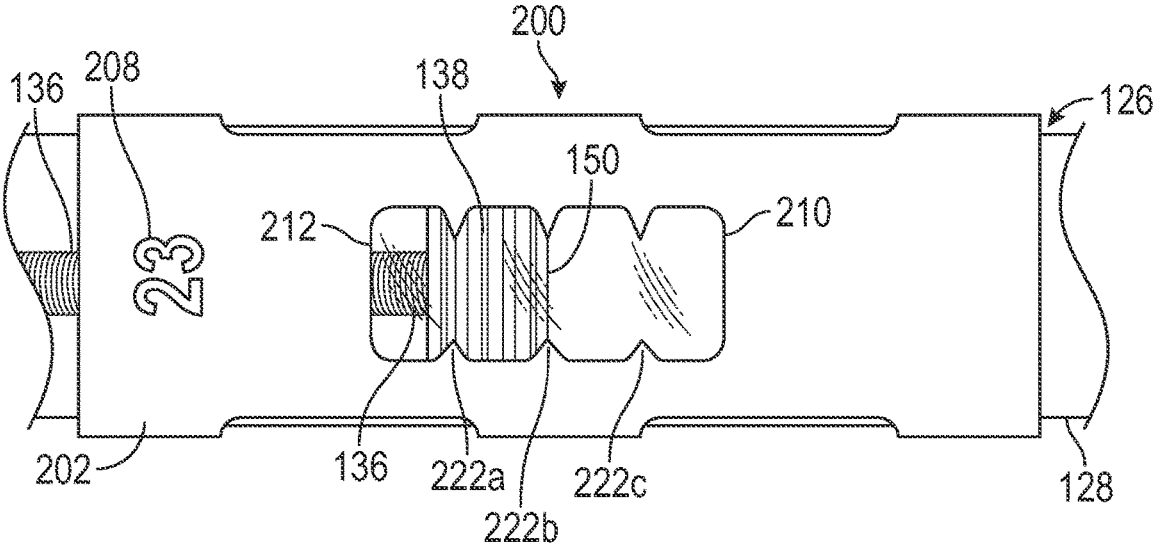
FIG. 8 is a front elevation view of an embodiment of a volume indicator disposed on the syringe of FIG. 3.

In use, when the volume indicator 200 of FIG. 8 is placed on a syringe 126, the syringe body 128 can be fully filled with fluid (e.g., using the method described above). To expand the prosthetic valve, once the syringe is coupled to the delivery apparatus the physician can actuate the plunger 134 of the syringe (e.g., by pushing it into the syringe body) until the end surface 150 of the plunger head 138 of the plunger 134 is aligned with the inflation indicator corresponding to the selected diameter, thus displacing the amount of fluid necessary to expand the prosthetic valve to the selected diameter. For example, to expand the prosthetic valve to a diameter of 21.5 mm, the physician can fully fill the syringe, fluidly connect the syringe to the delivery apparatus 100, deliver the prosthetic valve to the desired implantation site, and actuate the plunger until the end surface 150 of the plunger head 138 reaches inflation indicator 222a. This expands the prosthetic valve to the selected diameter. If further expansion of the prosthetic valve is required (e.g., from a 21.5 mm to 22.7 mm diameter), the plunger can be further actuated as described in detail below.

In one specific method for implanting a prosthetic heart valve in a patient's heart, a physician can select a prosthetic heart valve 10 having an expanded diameter range sized to accommodate a specific patient's anatomical variability (e.g., selecting the nominal size that is closest in size to the native annulus in which the prosthetic valve is to implanted). If needed, conventional techniques and/or devices can be used to measure the size of the native heart valve annulus in which the prosthetic heart valve will be implanted to facilitate selection of a properly sized prosthetic heart valve. Once the size of the prosthetic valve is selected (e.g., a 21-mm valve, a 23-mm valve, 26-mm valve, or a 29-mm valve), the physician can select a corresponding volume indicator 200 having inflation indicia 214 that correspond to the diameter range of that prosthetic valve.

Figure 6:
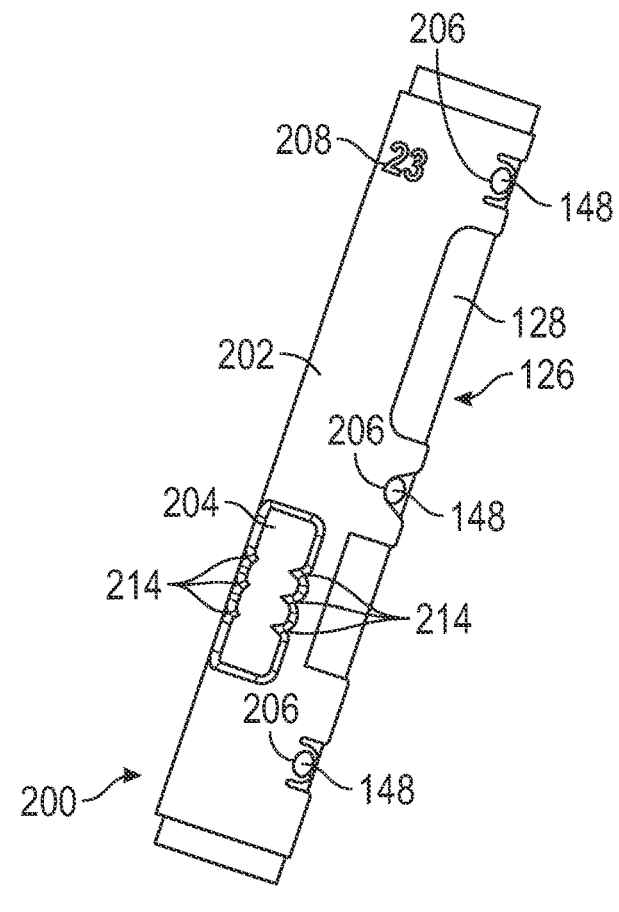
FIG. 6 is a perspective view of the volume indicator of FIG. 4A shown placed on the body the syringe of FIG. 3.

Referring now to FIG. 6, the selected volume indicator 200 can then be placed onto a syringe body 128 (e.g., by clipping or snapping the cover onto the syringe body). The second engagement elements 206 of the volume indicator can engage and form releasable connections with the first engagement elements 148 of the syringe body 128, thus retaining the volume indicator in place on the syringe body. Once the volume indicator 200 is attached to the syringe 126, the physician can fill the syringe body 128 with an inflation fluid (e.g., saline).

In embodiments wherein the volume of inflation fluid is measured from the first end 130 of the syringe body, during filling the end surface 150 of the plunger head 138 can be aligned with a selected inflation indicator 214 corresponding to the selected expanded valve diameter (see e.g., FIG. 7). In this way, the syringe body is filled with the appropriate amount of fluid needed to inflate the prosthetic heart valve 10 to the selected diameter. At this point, the volume indicator 200 can be removed from the syringe or kept in place for the remainder of the procedure.

Once filled, the syringe 126 can be fluidly coupled to the handle 102 of the delivery apparatus 100 at the proximal port 118, such as by connecting the tubing 144 to the proximal port 118. The prosthetic heart valve 10 can be mounted in a crimped configuration over balloon 116 on a distal end portion of the delivery apparatus 100. A representative method of implanting the prosthetic heart valve 10 using the delivery apparatus 100 can proceed in the following manner. The distal end portion of the delivery apparatus (along with the prosthetic valve 10) can be introduced into the patient's vasculature via, for example, an incision in the femoral artery. The distal end portion of the delivery apparatus 100 (along with the prosthetic valve 10) can be advanced through the femoral artery and the aorta toward the native aortic valve. Once the prosthetic heart valve 10 is positioned at the desired implantation location (typically within the native aortic annulus), the prosthetic heart valve can be deployed (e.g., radially expanded). Additional details regarding the implantation procedure can be found, for example, in U.S. Publication No. 2017/0065415.

To deploy the prosthetic valve 10, the physician can depress the plunger 134 of the syringe 126 such that the total volume of fluid within the syringe flows through the fluid passageway of the delivery apparatus and into the balloon 116 to inflate the same and deploy the prosthetic valve 10 to the selected diameter.

Referring to FIG. 8, in embodiments wherein the volume of inflation fluid is measured from the second end 132 of the syringe body 128, the syringe body can, for example, be fully filled with fluid such that the plunger head 138 of the plunger 134 is located at the second end 132. In this way, the syringe body is filled with enough fluid to sequentially expand the prosthetic valve 10 to each of the diameter sizes in the range of diameters for the prosthetic valve. Once fully filled, the syringe 126 can be fluidly coupled to the handle of the delivery apparatus and the prosthetic valve 10 can be advanced to the desired implantation location as described above.

Once the prosthetic heart valve 10 is at the desired implantation location, the prosthetic valve can be deployed to, for example, a first diameter in the range (e.g., the smallest diameter in the range) by depressing the plunger until the end surface 150 of the plunger head 138 aligns with the inflation indicator 222a indicating the first diameter. The physician may then evaluate the fit of the prosthetic valve within the native annulus. If further expansion of the prosthetic valve is required, the prosthetic valve can be expanded to, for example, the second diameter in the range by depressing the plunger until the end surface 150 of the plunger head 138 aligns with the inflation indicator 222b indicating the second diameter. This process can be repeated as necessary until the prosthetic valve is expanded to a diameter that best fits the native annulus. For example, the prosthetic valve 10 desirably is expanded to a diameter sufficient to anchor the prosthetic valve in place against the surrounding tissue with minimal or no paravalvular leakage and without over-expanding and rupturing the native annulus.

Figures 9, 10:
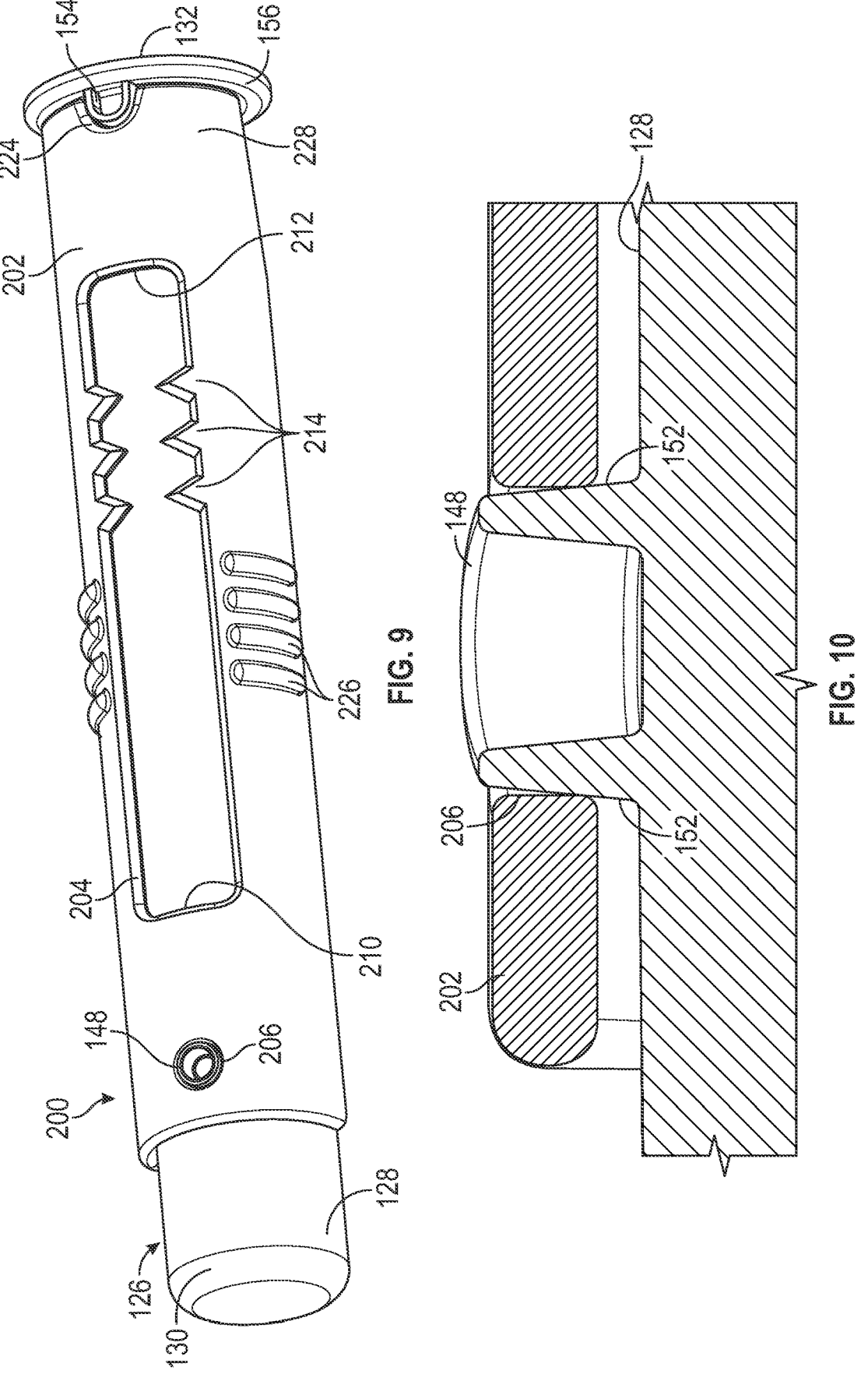
FIG. 9 is a perspective view of another embodiment of a volume indicator shown mounted on a syringe body.
FIG. 10 is a cross sectional view of a portion of the volume indicator of FIG. 9.

Referring now to FIGS. 9-10, in some embodiments, the volume indicator 200 can be clipped on to the syringe 126 using one or more second engagement elements 206 (e.g., one in the illustrated embodiment) configured as openings extending through the body 202 of the volume indicator 200. The syringe 126 can have one or more first engagement elements 148 (e.g., one in the illustrated embodiment) extending from a surface of the syringe body 128 and configured to engage the second engagement element 206. The second engagement element 206 can be, for example, a circular opening extending through the body 202 of the volume indicator 200, and the first engagement element 148 can be, for example, a cylindrical protrusion extending from the surface of the syringe body 128.

In some embodiments, as shown in FIG. 10, the first engagement element 148 can have a tapered external surface 152 configured to form an interference fit (e.g., a press-fit or a friction fit) with the second engagement element 206. This ensures that the first and second engagement elements 148, 206 form a tight or snug fit against one another such that the volume indicator 200 is restrained from moving or sliding with respect to the syringe body 128. The tapered surface 152 ensures that even if the second engagement element 206 is slightly oversized (e.g., due to manufacturing tolerances) there will be no looseness or sliding between the first and second engagement elements 148, 206, thus ensuring accurate placement of the volume indicator 200 and therefore the inflation indicia 214 axially along the syringe 126. This can help prevent inaccurate measurements based on incorrect placement of the volume indicator. In some embodiments, in lieu of or in addition to the tapering on the first engagement element 148, the second engagement element 206 can be configured as a tapered opening.

Referring again to FIG. 9, in some embodiments, the syringe body 128 can further comprise one or more additional engagement elements 154 extending from the surface of the syringe body 128 and located along, for example, the second end portion 132 of the syringe body 128. The volume indicator 200 can comprise one or more corresponding additional engagement elements 224 configured to engage the engagement elements 154. The engagement of the engagement elements 154, 224 can restrain the volume indicator 200 from rotational movement relative to the syringe body 128 when the volume indicator is clipped onto the syringe body. As shown, the engagement element 224 can be U-shaped notch formed along the proximal edge of the indicator body 202 adjacent the lip 156 and the engagement element 154 can comprise a corresponding U-shaped projection extending from the lip 156.

It should be noted that, while in the illustrated embodiment the engagement element 224 is a U-shaped notch opening configured to receive a correspondingly U-shaped engagement element 154 of the syringe body 128, in other embodiments, the one or more second engagement elements 224 can be any of various sizes and shapes (e.g., circular, rectangular, triangular, etc.) configured to mate with correspondingly shaped one or more engagement elements 154.

In some embodiments, aligning the engagement elements 154, 224 aligns the volume indicator 200 over the syringe 126 such that the engagement elements 148, 206 are positioned to engage one another. This allows a user to quickly and easily clip the volume indicator 200 onto the syringe 126 in the correct orientation.

The window portion 204 in the embodiment of FIG. 9 is longer than the window portion 204 in the embodiment of FIG. 6. Thus, the opposing edges 210, 212 of the window portion in the embodiment of FIG. 9 are spaced farther from the volume indicia 214 than in the embodiment of FIG. 6. This can help to avoid a user using one of the opposing edges 210, 212 to measure fluid when the edges 210, 212 are not intended to be used as volume indicia. In certain embodiments, the length $L_2$ of the window portion 204 can be greater than a majority of the length of the indicator body $L_1$ to maximize the spacing between the volume indicia 214 and the opposing edges 210, 212. However, in alternative embodiments, the indicator can be manufactured such that one or both edges 210, 212 are positioned to serve as volume indicia for measuring an amount of fluid for expanding a prosthetic valve to a desired size.

In embodiments wherein the proximal port 118 comprises a stopcock, prior to actuating the plunger 134 the physician can actuate the stopcock from the closed position to the open position such that fluid from the fluid source can flow through the stopcock and into the fluid passageway of the delivery apparatus 100.

Although the disclosed embodiments pertain generally to delivery apparatuses and methods for implantation of prosthetic heart valves in the native aortic valve, it should be understood that the disclosed embodiments can be used implant prosthetic devices at any location of the heart or elsewhere in the body. Additionally, although the disclosed embodiments pertain generally to transfemoral delivery of prosthetic devices, it should be understood that the disclosed embodiments can be adapted for use with, for example, transapical procedures, transaortic procedures, trans-subclavian procedures, transradial procedures, or trans-septal procedures.

General Considerations

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

All features described herein are independent of one another and, except where structurally impossible, can be used in combination with any other feature described herein. For example, a volume indicator can comprise the window portion 204 as shown in FIGS. 4A-4C in combination with the first and second engagement elements 148, 206 as shown in FIGS. 9-10. In another embodiment, a volume indicator can comprise the window portion 204 as shown in FIGS. 9-10 in combination with the first and second engagement elements 148, 206 as shown in FIGS. 4A-4C.

As used in this application and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, and/or physically (e.g., mechanically or chemically) coupled or linked and does not exclude the presence of intermediate elements between the coupled or associated items absent specific contrary language.

In the context of the present application, the terms "lower" and "upper" are used interchangeably with the terms "inflow" and "outflow", respectively. Thus, for example, the lower end of the valve is its inflow end and the upper end of the valve is its outflow end.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device toward the user, while distal motion of the device is motion of the device away from the user. The terms "longitudinal" and "axial" refer to an axis extending in the proximal and distal directions, unless otherwise expressly defined.

In view of the many possible embodiments to which the principles of the disclosure may be applied, it should be recognized that the illustrated embodiments are only preferred examples and should not be taken as limiting the scope of the disclosure. Rather, the scope of the disclosure is defined by the following claims.

The invention claimed is:

1. A method comprising:
placing a volume indicator on a syringe comprising a syringe body by seating an engagement element on the syringe body within a corresponding engagement element that extends from an inner surface of the volume indicator laterally outwardly into a wall of the volume indicator, the syringe comprising the syringe body and a plunger received in the syringe body and the volume indicator comprising an indicator body and volume indicia on the indicator body, wherein the engagement element on the syringe body comprises a protrusion extending from a surface of the syringe body;
filling the syringe body with an amount of fluid corresponding to one of the volume indicia on the indicator body; and
fluidly connecting the syringe to a delivery apparatus for a prosthetic valve.

2. The method of claim 1, wherein the engagement element on the syringe body is a first engagement element and the corresponding engagement element on the volume indicator is a first corresponding engagement element, and wherein the act of placing the volume indicator on the syringe comprises further engaging a second engagement element on the syringe body with a second corresponding engagement element on the indicator body.

3. The method of claim 1, further comprising inserting into a body of a patient a distal end portion of the delivery apparatus and a prosthetic heart valve mounted in a radially compressed configuration on a balloon mounted on the distal end portion of the delivery apparatus.

4. The method of claim 3, further comprising:

advancing the distal end portion of the delivery apparatus and the radially compressed prosthetic valve through the patient's vasculature to position the prosthetic valve at a selected implantation area; and actuating the plunger of the syringe to inject the fluid into the balloon, thereby inflating the balloon and radially expanding the prosthetic heart valve.

5. The method of claim 3, wherein the prosthetic heart valve can be expanded to an expanded functional diameter within a range of expanded diameters, and wherein the act of filling the syringe body comprises selecting a fill volume needed to expand the prosthetic heart valve to a selected expanded diameter within the range of expanded diameters.

6. The method of claim 1, wherein the volume indicia on the indicator body are not aligned with volume indicia on the syringe body when the volume indicator is placed on the syringe.

7. The method of claim 1, wherein the volume indicator is selected from a kit of volume indicators.

8. The method of claim 7, wherein each volume indicator in the kit corresponds to a different nominal valve size.

9. The method claim 7, wherein the volume indicator is a first volume indicator corresponding to a prosthetic heart valve having a nominal size of 20 mm, and wherein the kit further comprises a second volume indicator corresponding to a prosthetic heart valve having a nominal size of 23 mm, a third volume indicator corresponding to a prosthetic heart valve having a nominal size of 26 mm, and a fourth volume indicator corresponding to a prosthetic heart valve having a nominal size of 29 mm.

10. The method of claim 1 wherein the volume indicator comprises a window portion extending through a thickness of the indicator body such that a portion of the syringe plunger in the syringe body is visible through the window portion.

11. The method of claim 10 wherein the volume indicator further comprises inflation indicia adjacent the window portion.

12. The method of claim 10, wherein the volume indicator further comprises inflation indicia comprising protrusions extending at least partially across the window portion.

13. The method of claim 1, wherein the corresponding engagement element on the volume indicator is an opening that extends from an inner surface of the volume indicator laterally into a thickness of the wall of the volume indicator and wherein the engagement element on the syringe body is a projection that extends laterally from a surface of the syringe body, the projection having a circular shape in cross-section.

14. A method for using a volume indicator with a syringe for inflating a balloon to expand a prosthetic heart valve, the method comprising:

placing a volume indicator on a syringe by engaging first and second engagement elements of a syringe body with first and second corresponding engagement elements of the volume indicator, the syringe comprising a syringe body and a plunger received in the syringe body and the volume indicator comprising an indicator body and volume indicia on the indicator body, wherein the first corresponding engagement element is disposed at a first end portion of the indicator body and wherein the second corresponding engagement element is disposed at a second end portion of the indicator body;

filling the syringe body with an amount of fluid corresponding to one of the volume indicia on the indicator body; and fluidly connecting the syringe to a delivery apparatus for a prosthetic valve.

15. The method of claim 14, wherein the first and second engagement elements of the syringe body are protrusions extending from a surface of the syringe body and wherein the first and second corresponding engagement elements are openings extending into the thickness of the indicator body.

16. The method of claim 14, further comprising inserting into a body of a patient a distal end portion of the delivery apparatus and a prosthetic heart valve mounted in a radially compressed configuration on a balloon mounted on the distal end portion of the delivery apparatus.

17. The method of claim 16, further comprising:

advancing the distal end portion of the delivery apparatus and the radially compressed prosthetic valve through the patient's vasculature to position the prosthetic valve at a selected implantation area; and actuating the plunger of the syringe to inject the fluid into the balloon, thereby inflating the balloon and radially expanding the prosthetic heart valve.

18. The method of claim 16, wherein the prosthetic heart valve can be expanded to an expanded functional diameter within a range of expanded diameters, and wherein the act of filling the syringe body comprises selecting a fill volume needed to expand the prosthetic heart valve to a selected expanded diameter within the range of expanded diameters.

19. The method of claim 14, wherein the volume indicia on the indicator body are not aligned with volume indicia on the syringe body when the volume indicator is placed on the syringe.

20. The method of claim 14, wherein the volume indicator is selected from a kit of volume indicators.

21. A method for using a volume indicator with a syringe for inflating a balloon to expand a prosthetic heart valve, the method comprising:

placing a volume indicator on a syringe by engaging first and second engagement elements of a syringe body with first and second corresponding engagement elements of the volume indicator, the syringe comprising a syringe body and a plunger received in the syringe body and the volume indicator comprising an indicator body and volume indicia on the indicator body, wherein the first corresponding engagement element is disposed at a first end portion of the indicator body and wherein the second corresponding engagement element is disposed at a second end portion of the indicator body;

filling the syringe body with an amount of fluid corresponding to one of the volume indicia on the indicator body;

fluidly connecting the syringe to a delivery apparatus for a prosthetic valve; and wherein the volume indicator is a first volume indicator selected from a kit of volume indicators, the first volume indicator corresponding to a prosthetic heart valve having a nominal size of 20 mm, and wherein the kit comprises a second volume indicator corresponding to a prosthetic heart valve having a nominal size of 23 mm, a third volume indicator corresponding to a prosthetic heart valve having a nominal size of 26 mm, and a fourth volume indicator corresponding to a prosthetic heart valve having a nominal size of 29 mm.

* * * * *